(12) United States Patent
Aoki et al.

(10) Patent No.: US 6,927,230 B2
(45) Date of Patent: Aug. 9, 2005

(54) TRIAZOLE DERIVATIVES

(75) Inventors: Satoshi Aoki, Osaka (JP); Toshiya Nakagawa, Osaka (JP); Nobukiyo Konishi, Osaka (JP); Katsuya Nakamura, Osaka (JP); Hiroki Omori, Osaka (JP); Ariyoshi Kubota, Osaka (JP); Norio Hashimoto, Osaka (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/344,416
(22) PCT Filed: Oct. 30, 2002
(86) PCT No.: PCT/JP02/11314
§ 371 (c)(1), (2), (4) Date: Feb. 19, 2003
(87) PCT Pub. No.: WO03/040110
PCT Pub. Date: May 15, 2003

(65) Prior Publication Data
US 2003/0191155 A1 Oct. 9, 2003

(30) Foreign Application Priority Data
Nov. 9, 2001 (AU) ............................... PR8782

(51) Int. Cl.⁷ .................. A61K 31/4196; C07D 249/12
(52) U.S. Cl. .................. 514/384; 548/264.2; 548/264.4
(58) Field of Search ....................... 514/384; 548/264.2, 548/264.4

(56) References Cited

FOREIGN PATENT DOCUMENTS

| EP | 0 051 084 | 5/1982 |
|---|---|---|
| EP | 0 155 486 | 9/1985 |
| EP | 0 157 259 | 10/1985 |
| EP | 0 162 217 | 11/1985 |
| JP | 60 233068 | 11/1985 |
| WO | 99/51580 | 10/1999 |
| WO | 00 10563 | 3/2000 |

OTHER PUBLICATIONS

Geza Szilagyi et al.; "Preparation and antiarthritic activity of new 1,5–diaryl–3–(alkylthio)–1H 1,2,4–triazoles and corresponding sulfoxides and sulfones" European Journal of Medicinal Chemistry, vol. 25, No. 2, pp. 95–101, 1990.

L. Czollner et al.: "1,2,4–triazoles, II 1 synthesis of 1,5–diphenyl–3–trifluoromethl–1H–1,2,4–triazoles" Monatshefte Fur Chemie, vol. 119, pp. 349–353 1988.

*Primary Examiner*—Patricia L. Morris
(74) *Attorney, Agent, or Firm*—Oblon, Spivak, McClelland, Maier & Neustadt, P.C.

(57) ABSTRACT

A compound of the formula (I):

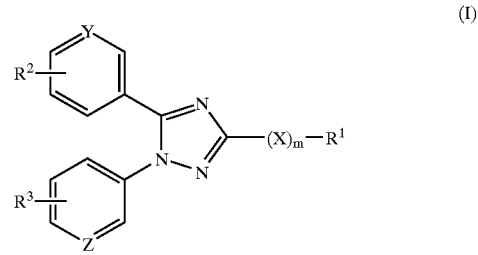

wherein $R^1$ is lower alkyl which is optionally substituted with
  halogen, cyano,
  N,N-di(lower)alkylcarbamoyl,
  phenyl optionally substituted with halogen, or heterocyclic group,
  cyclo(lower)alkyl,
  lower alkynyl, or
  N,N-di(lower)alkylcarbamoyl;
$R^2$ is lower alkyl, lower alkoxy, cyano, or 1H-pyrrol-1-yl;
$R^3$ is lower alkyl, lower alkoxy, or cyano;
X is O, S, SO or $SO_2$;
Y and Z are each CH or N; and
m is 0 or 1;
or salts thereof, which are useful as a medicament.

10 Claims, No Drawings

TRIAZOLE DERIVATIVES

TECHNICAL FIELD

This invention relates to triazole compounds having pharmacological activity, to a process for their production and to a pharmaceutical composition containing the same.

BACKGROUND ART

The presence of two cyclooxygenase isoenzymes, cyclooxygenase-I (COX-I) and cyclooxygenase-II (COX-II) is known (Proc. Nat. Acad. Sci. USA 88, 2692–2696 (1991)).

Traditional non steroidal anti-inflammatory compounds (NSAIDs) have inhibiting activities of both COX-I and COX-II (J. Biol. Chem., 268, 6610–6614 (1993), etc). The therapeutic use thereof involves undesired effects on the gastrointestinal tract, such as bleeding, erosions, gastric and intestinal ulcers, etc.

It was reported that selective inhibition of COX-II shows anti-inflammatory and analgesic activities comparable with conventional NSAIDs but with a lower incidence of some gastrointestinal undesired effects (Pro. Nat. Acad. Sci. USA, 91, 3228–3232(1994)). Accordingly, various selective COX-II inhibitors have been prepared. However, it was reported that those "selective COX-II inhibitor" show some side-effects on kidney and/or insufficient efficacy on acute pains.

Further, some compounds such as SC-560, mofezolac, etc, which have certain selective inhibiting activity against COX-I. WO98/57910 shows some compounds having such activity. However, their selectivity of inhibiting COX-I does not seem to be enough to use them as a clinically acceptable and satisfactory analgesic agent due to their gastrointestinal disorders.

WO02/055502 shows some pyridine derivatives having cyclooxygenase inhibiting activity, particularly cyclooxygenase-I inhibiting activity. And WO99/51580 shows some triazole derivatives having an inhibiting activity of cytokine production.

DISCLOSURE OF INVENTION

This invention relates to triazole compounds, which have pharmaceutical activity such as cyclooxygenase (hereinafter described as COX) inhibiting activity, to a process for their production, to a pharmaceutical composition containing the same and to a use thereof.

Accordingly, one object of this invention is to provide the triazole compounds, which have a COX inhibiting activity.

Another object of this invention is to provide a process for production of the triazole compounds.

A further object of this invention is to provide a pharmaceutical composition containing, as active ingredients, the triazole compounds.

Still further object of this invention is to provide a use of the triazole compounds for manufacturing a medicament for treating or preventing various diseases.

The new triazole compounds of this invention can be represented by the following general formula (I):

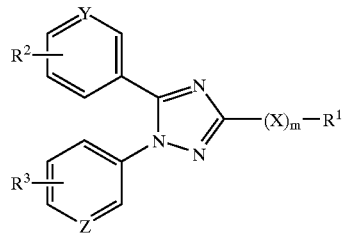

wherein $R^1$ is lower alkyl which is optionally substituted with halogen, cyano, N,N-di(lower)alkylcarbamoyl, phenyl optionally substituted with halogen, or heterocyclic group, cyclo(lower)alkyl, lower alkynyl, or N,N-di(lower)alkylcarbamoyl;

$R^2$ is lower alkyl, lower alkoxy, cyano, or 1H-pyrrol-1-yl;

$R^3$ is lower alkyl, lower alkoxy, or cyano;

X is O, S, SO or $SO_2$;

Y and Z are each CH or N; and m is 0 or 1;

or salts thereof.

The object compound (I) of the present invention can be prepared by the following processes.

Process (1)

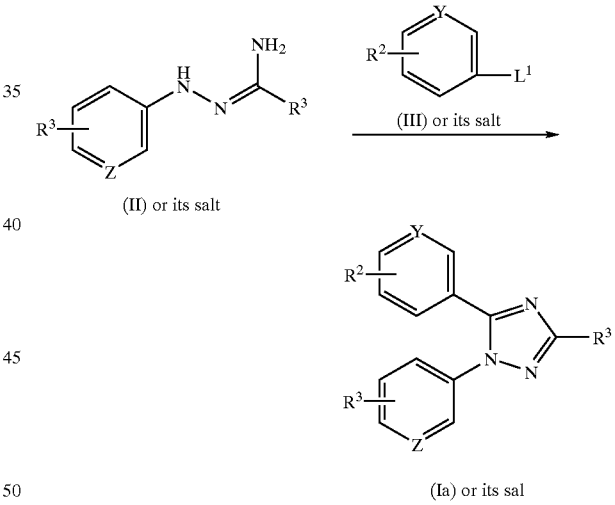

Process (2)

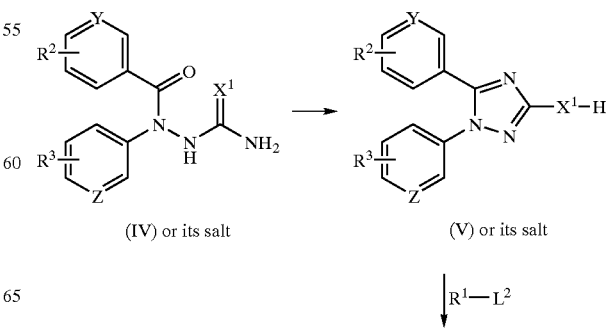

Process (5)

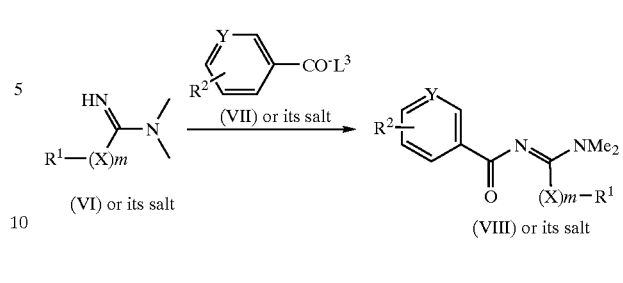

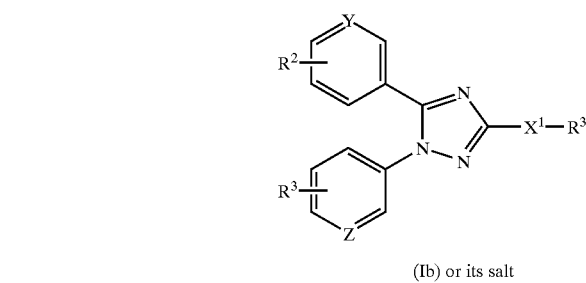

(Ib) or its salt

Process (3)

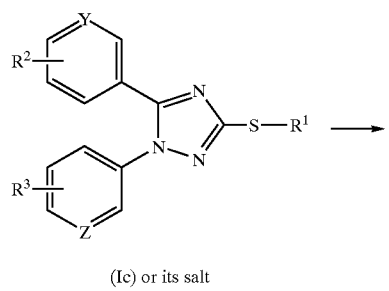

(Ic) or its salt

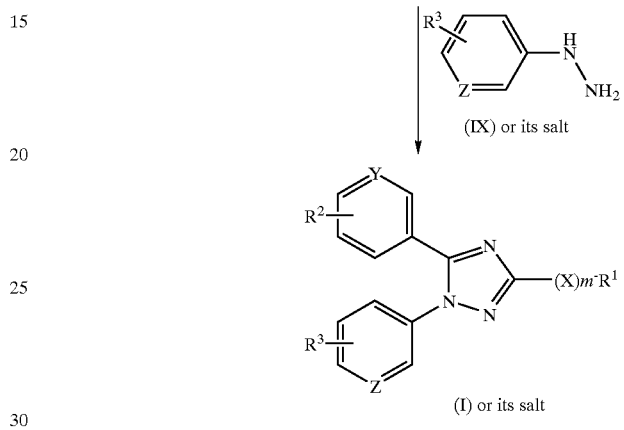

(I) or its salt (Id) or its sal

Process (4)

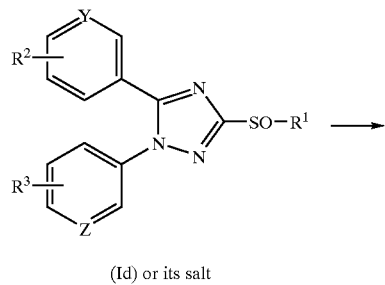

(Id) or its salt

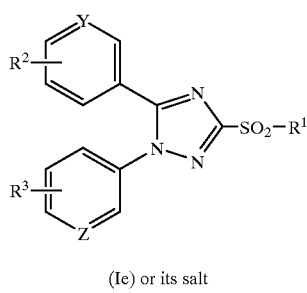

(Ie) or its salt

In the above processes, $R^1$, $R^2$, $R^3$, X, Y, Z and m are each as defined above, and $X^1$ is O or S, and $L^1$, $L^2$ and $L^3$ are each a leaving group.

The compounds of formula (I), (Ia), (Ib), (Ic), (Id), (Ie) or (If) may contain one or more asymmetric centers and thus they can exist as enantiomers or diastereoisomers. This invention includes both mixtures and separate individual isomers.

The compounds of the formula (I), (Ia), (Ib), (Ic), (Id), (Ie) or (If) may also exist in tautomeric forms and the invention includes both mixtures and separate individual tautomers.

The compounds of the formula (I), (Ia), (Ib), (Ic), (Id), (Ie) or (If) and its salts can be in a form of a solvate, which is included within the scope of the present invention. The solvate preferably include a hydrate and an ethanolate.

Also included in the scope of invention are radiolabelled derivatives of compounds of formula (I), (Ia), (Ib), (Ic), (Id), (Ie) or (If) which are suitable for biological studies.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "lower alkyl", and lower alkyl moiety in the term "lower alkoxy" may be a straight or branched one, such as methyl, ethyl, propyl, isopropyl, butyl, isobutyl, tert-butyl, pentyl, hexyl or the like, in which preferable one is methyl or dimethyl.

Suitable lower alkoxy is methoxy, ethoxy, propoxy, isopropoxy, butoxy, isobutoxy, tert-butoxy, pentoxy, hexoxy, or the like, in which preferable one is methoxy.

Suitable "halogen" may be fluoro, chloro, bromo or iodo or the like, which preferable one is fluoro.

Suitable "lower alkyl substituted with halogen" may be lower alkyl substituted with one or more halogen atoms(s), such as fluoromethyl, difluoromethyl, trifluoromethyl, chloromethyl, dichloromethyl, trichloromethyl, bromomethyl, dibromomethyl, tribromomethyl, fluoroethyl, chloroethyl, 2,2,2-trifluoroethyl, 2,2,2-trichloroethyl, 2,2,3,3,3-pentafluoroethyl, fluoropropyl, fluorobutyl, fluorohexyl, or the like. And its preferable one is halogen-substituted C1–C2 alkyl. More preferable one is fluorine-substituted methyl, and most preferable one is trifluoromethyl or 2,2,2-trifluoroethyl.

Suitable "cyclo(lower)alkyl" may include 3 to 8-membered cycloalkyl such as cyclopropyl, cyclobutyl, cyclopentyl, cyclohexyl, cycloheptyl, cyclooctyl, and the like, preferably one having 5 to 7 carbon atoms.

Suitable "N,N-di(lower)alkylcarbamoyl" may be a carbamoyl group substituted with the same or different above lower alkyl groups on nitrogen atom, such as dimethylcarbamoyl, diethylcarbamoyl, dipropylcarbamoyl, diisopropylcarbamoyl, or the like. It is preferably di(C1–C4) carbamoyl, more preferably di(C1–C2 alkyl)carbamoyl.

Suitable "heterocyclic group" may be saturated or unsaturated, monocyclic or polycyclic heterocyclic group containing at least one hetero-atom such as an oxygen, sulfur, nitrogen atom and the like. And, especially preferable heterocyclic group may be heterocyclic group such as unsaturated 3 to 8-membered more preferably 5 or 6-membered heteromonocyclic group containing 1 to 4-nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, tetrahydropyridazinyl (e.g. 2,3,4,5-tetrahydropyridazinyl, etc.), triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example pyrrolidinyl, imidazolidinyl, piperidino, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl (e.g. 3-isoxazolyl), oxadiazolyl (e.g. 1,2,4-oxadiazolyl, 1,3,4-oxadiazolyl, 1,2,5-oxadiazolyl, etc.) etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl (e.g., 1,3-thiazolyl), isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteramonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 to 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

Suitable leaving group may be a halogen, such as chloride, etc.

Suitable alkynyl may be a monovalent branched or unbranched hydrocarbon radical containing at least one carbon-carbon triple bond, for example ethynyl, 2-propynyl, 2-butynyl, and the like.

Preferable combination of Y and Z is a CH and CH, CH and N, or N and CH.

Preferable (I) may be the following (I').

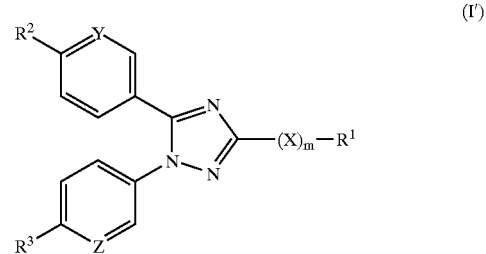

wherein $R^1$ is lower alkyl,
lower alkyl substituted with halogen, cyano,
N,N-di(lower)alkylcarbamoyl,
phenyl optionally substituted with halogen, or heterocyclic group,
cyclo(lower)alkyl,
lower alkynyl, or
N,N-di(lower)alkylcarbamoyl;
$R^2$ is lower alkyl, lower alkoxy, cyano, or 1H-pyrrol-1-yl;
$R^3$ is lower alkyl, lower alkoxy, or cyano;
X is O, S, SO or $SO_2$; Y and Z are each CH or N; and
m is 0 or 1;
or salts thereof.

Among the above compound (I'), the more preferable one is as follows.
$R^1$ is lower alkyl or lower alkyl substituted with halogen;
$R^2$ is lower alkoxy; $R^3$ is lower alkoxy;
X is O; Y and Z are each CH; and m is 1.

Suitable salts of the compounds (I) are pharmaceutically acceptable conventional non-toxic salts and include a metal salt such as an alkali metal salt (e.g., sodium salt, potassium salt, etc.) and an alkaline earth metal salt (e.g., calcium salt, magnesium salt, etc.), an ammonium salt, an organic base salt (e.g., trimethylamine salt, triethylamine salt, pyridine salt, picoline salt, dicyclohexylamine salt, etc.), an organic acid salt (e.g., acetate, maleate, tartrate, methanesulfonate, benzenesulfonate, formate, toluenesulfonate, trifluoroacetate, etc.), an inorganic acid salt (e.g., hydrochloride, hydrobromide, sulfate, phosphate, etc.), a salt with an amino acid (e.g., arginine, aspartic acid, glutamic acid, etc.), or the like.

The processes for preparing the object compounds are explained in detail in the following.

Process (1)

The compound (Ia) or a salt thereof can be prepared by reacting the compound (II) or a salt thereof with the compound (III) or a salt thereof.

The reaction is usually carried out in a conventional solvent such tetrahydrofuran, dioxane, chloroform, methylene chloride, dimethyl acetamide, N,N-dimethylformamide or any other organic solvent which does not adversely influence the reaction.

This reaction is preferably carried out in the presence of an inorganic or an organic base such as an alkali metal hydroxide, an alkali metal hydrogencarbonate, alkali metal carbonate, alkali metal acetate, tri(lower)alkylamine, pyridine (e.g. pyridine, lutidine, picoline, dimethylaminopyridine, etc.), N-(lower)alkylmorpholine, N-,N-di(lower)alkylbenzylamine, N-,N-di (lower) alkylaniline or the like. When the base, the acid and/or the starting compound are in liquid, they can be used also as a solvent.

The reaction temperature is not critical and the reaction is usually carried out under cooling to heating.

Process (2)

The compound (V) or a salt thereof can be prepared by converting the compound (IV) or a salt thereof under basic condition.

The reaction is usually carried out in a conventional solvent such as water, alcohols (e.g., methanol, ethanol, isopropyl alcohol, etc.), tetrahydrofuran, dioxane, chloroform, methylene chloride, dimethyl acetamide, N,N-dimethylformamide or any other organic solvent which does not adversely influence the reaction. Among these solvents, hydrophilic solvents may be used in a mixture with water.

This reaction is preferably carried out in the presence of an inorganic or an organic base such as an alkali metal hydroxide, an alkali metal hydrogencarbonate, alkali metal carbonate, alkali metal acetate, tri(lower)alkylamine, pyridine (e.g. pyridine, lutidine, picoline, dimethylaminopyridine, etc.), N-(lower)alkylmorpholine, N-,N-di(lower)alkylbenzylamine, N-,N-di(lower) alkylaniline or the like. When the base, the acid and/or the starting compound are in liquid, they can be used also as a solvent.

The reaction temperature is not critical and the reaction is usually carried out under cooling to heating.

Subsequently, the obtained compound (V) is condensed with $R^1$-$L^2$ under basic condition to give a compound (Ib).

The reaction is usually carried out in a conventional solvent as exemplified in Process 1, or any other organic solvent which does not adversely influence the reaction. Among these solvents, hydrophilic solvents may be used in a mixture with water.

The suitable base may include a tertiary amine [e.g. triethylamine, pyridine, N,N-dimethylaniline, etc.], an alkali metal hydroxide [e.g. sodium hydroxide, potassium hydroxide, etc.], an alkalimetal carbonate [e.g. sodium carbonate, potassium carbonate, etc.], alkali metal bicarbonate (e.g. sodium bicarbonate, etc.), a salt of an organic acid [e.g. sodium acetate, etc.] and the like. In case that the base is liquid, the base can be used as a solvent.

The reaction temperature is not critical and the reaction is usually carried out under cooling to warming.

Process (3)

The compound (Id) or a salt thereof can be prepared by reacting the compound (Ic) with an oxidizing agent.

The reaction is usually carried out in a conventional solvent as exemplified in Process 1, or any other organic solvent, which does not adversely influence the reaction. Among these solvents, hydrophilic solvents may be used in a mixture with water.

The suitable oxidizing agent may include a hydrogen peroxide, cumene hydroperoxide, tert-butyl hydroperoxide, Jones reagent, per acid [e.g. peracetic acid, perbenzoic acid, m-chloroperbenzoic acid, monopersulfate compound (Oxone) etc.)], chromic acid, potassium permanganate, alkali metal periodate [e.g. sodium periodate, etc.], and the like.

The reaction temperature is not critical and the reaction is usually carried out under cooling to warming.

Process (4)

The compound (Ie) or a salt thereof can be prepared by reacting the compound (Id) with an oxidizing agent.

The reaction is usually carried out in a conventional solvent as exemplified in Process (3), or any other organic solvent, which does not adversely influence the reaction.

The oxidizing agent employable in this process is a conventional reagent as exemplified in Process (3).

The reaction temperature is not critical and the reaction is usually carried out under cooling to warming.

Process (5)

Compound (VIII) or a its salt can be prepared by the reaction of compound (VI) or a its salt with compound (VII) or a its salt under basic condition.

The reaction is usually carried out in a suitable solvent such as acetates, tetrahydrofuran, dioxane, chloroform, methylene chloride, dimethyl acetamide, N,N-dimethylformamide or any other organic solvent which does not affect the reaction.

This reaction is preferably carried out in the presence of an inorganic or an organic base such as an alkali metal hydrogencarbonate, alkali metal carbonate, alkali metal acetate, trialkylamine, pyridine (e.g. pyridine, lutidine, picoline, dimethylaminopyridine, etc.), N-alkylmorpholine, N-,N-dialkylbenzylamine, N-,N-dialkylaniline and so on. In case base, acid and/or starting compound are liquid, they can play a role of solvent.

The reaction temperature is not critical to the reaction in the yield or purity and the reaction is allowed to be carried out independent of temperature.

Subsequently, compound (VIII) or a its salt is reacted with compound (IX) or a its salt under acidic condition to give a compound (I) or its salt. When a salt of compound (IX) is used in this reaction, a suitable base may be added to neutralize the system.

The reaction is usually carried out in a suitable solvent such as water, acetic acid, methanol, tetrahydrofuran, dioxane, chloroform, methylene chloride, dimethyl acetamide, N,N-dimethylformamide or any other organic solvent which does not affect the reaction. In addition, a mixed solvent is allowed to be used.

The suitable acid may include an organic carboxylic acid [e.g. formic acid, acetic acid, propionic acid, etc.), an organic sulfonic acid [e.g. methane sulfonic acid, benzenesulfonic acid, p-toluenesulfonic acid, etc.], a mineral acid [e.g. hydrochloric acid, sulfuric acid, etc.]. In case where the acid is liquid, it can play a role of solvent.

The reaction temperature is not critical to the reaction in the yield or purity and the reaction is allowed to be carried out independent of temperature.

In order to illustrate the usefulness of the object compounds (I), the pharmacological test data of the compounds (I) are shown in the following.

[A] Analgesic Activity:
Effect on Adjuvant Arthritis in Rats:
(i) Test Method:
Arthritis was induced by injection of 0.5 mg of *Mycobacterium tuberculosis* (Difco Laboratories, Detroit, Mich.) in 50 µl of liquid paraffin into the right hind footpad of Lewis rats aged 7 weeks. Analgesic activity of a single dose of agents in arthritic rats was studied. Arthritic rats were randomized and grouped (n=10) for drug treatment based on pain threshold of left hind paws and body weight on day 22. Drugs (Test compounds) were administered and the pain threshold was measured 2 hr after drug administration. The intensity of hyperalgesia was assessed by the method of Randall-Selitto. The mechanical pain threshold of the left hind paw (uninjected hind paw) was determined by compressing the ankle joint with a balance pressure apparatus (Ugo Basile Co. Ltd., Varese, Italy). The threshold pressure of rats squeaking or struggling was expressed in grams. The threshold pressure of rats treated with drugs was compared with that of non-treated rats. A dose showing the ratio of 1.5 is considered to be the effective dose.
(ii) Test Results:

| Test compound (Example No.) | Dose (mg/kg) | The coefficient of analgesic |
|---|---|---|
| 1(2) | 3.2 | >=1.5 |
| 5(4) | 3.2 | >=1.5 |
| 25 | 3.2 | >=1.5 |

[B] Inhibiting Activity Against COX-I and COX-II (Whole Blood Assay):
(i) Test Method:
Whole Blood Assay for COX-I
Fresh blood was collected by syringe without anticoagulants from volunteers with consent. The subjects had no apparent inflammatory conditions and had not taken any medication for at least 7 days prior to blood collection. 500 µl aliquots of human whole blood were immediately incubated with 2 µl of either DMSO vehicle or a test compound at final concentrations for 1 hr at 37 C. to allow the blood to clot. Appropriate treatments (no incubation) were used as blanks. At the end of the incubation, 5 µl of 250 mM Indomethacin was added to stop the reaction. The blood was centrifuged at 6000×g for 5 min at 4 C to obtain serum. A 100 µl aliquot of serum was mixed with 400 µl methanol for protein precipitation. The supernatant was obtained by centrifuging at 6000×g for 5 min at 4 C and was assayed for TXB2 using an enzyme immunoassay kit according to the manufacturer's procedure. For a test compound, the results were expressed as percent inhibition of TXB2 production relative to control incubations containing DMSO vehicle. The data were analyzed by that a test compound at the indicated concentrations was changed log value and was applied simple linear regression. IC50 value was calculated by least squares method.
Whole Blood Assay for COX-II
Fresh blood was collected in heparinized tubes by syringe from volunteers with consent. The subjects had no apparent inflammatory conditions and had not taken any medication for at least 7 days prior to blood collection. 500 µl aliquots of human whole blood were incubated with either 2 µl DMSO vehicle or 2 µl of a test compound at final concentrations for 15 min at 37 C This was followed by incubation of the blood with 10 µl of 5 mg/ml lipopolysaccharide for 24 hr at 37 C for induction of COX-2. Appropriate PBS treatments (no LPS) were used as blanks. At the end of the incubation, the blood was centrifuged at 6000×g for 5 min at 4 C to obtain plasma. A 100 µl aliquot of plasma was mixed with 400 µl methanol for protein precipitation. The supernatant was obtained by centrifuging at 6000×g for 5 min at 4 C and was assayed for PGE2 using a radioimmunoassay kit after conversion of PGE2 to its methyl oximate derivative according to the manufacturer's procedure. For a test compound, the results were expressed as percent inhibition of PGE2 production relative to control incubations containing DMSO vehicle. The data were analyzed by that a test compound at the indicated concentrations was changed log value and was applied simple linear regression. IC50 value was calculated by least squares method.
(ii) Test Results:

| Test compound (Example No.) | COX-I IC50 ($\mu$M) | COX-II IC50 ($\mu$M) |
|---|---|---|
| 1(2) | <0.01 | >0.1 |
| 5(4) | <0.01 | >0.1 |
| 6(4) | <0.01 | >0.1 |
| 6(6) | <0.01 | >0.1 |
| 8 | <0.01 | >0.1 |
| 12(2) | <0.01 | >0.1 |
| 13 | <0.01 | >0.1 |
| 15-(4) | <0.01 | >0.1 |
| 16 | <0.01 | >0.1 |
| 17 | <0.01 | >0.1 |
| 19 | <0.01 | >0.1 |
| 20 | <0.01 | >0.1 |
| 21 | <0.01 | >0.1 |
| 23 | <0.01 | >0.1 |
| 24 | <0.01 | >0.1 |
| 25 | <0.01 | >0.1 |
| 26 | <0.01 | >0.1 |

It appeared, from the above-mentioned Test Results, that the compound (I) or pharmaceutically acceptable salts thereof of the present invention have an inhibiting activity against COX, particularly a selective inhibiting activity against COX-I.
[C] Inhibiting Activity on Aggregation of Platelet
(i) Methods
Preparation of Platelet-rich Plasma
Blood from healthy human volunteers was collected into plastic vessels containing 3.8% sodium citrate (1/10 volume). The subject had no taken any compounds for at least seven days prior to blood collection. Platelet-rich plasma was obtained from the supernatant fraction of blood after centrifugation at 1200 r.p.m. for 10 min. Platelet-poor plasma was obtained by centrifugation of the remaining blood at 3000 r.p.m. for 10 min.
Measurement of Platelet Aggregation
Platelet aggregation was measured according to the turbidimetric method with an aggregometer (Hema Tracer). In the cuvette, platelet-rich plasma was pre-incubated for 2 min at 37 C after the addition of compounds or vehicle. In order to quantify the inhibitory effects of each compound, the maximum increase in light transmission was determined from the aggregation curve for 7 min after the addition of agonist. We used collagen as agonist of platelet aggregation in this study. The final concentration of collagen was 0.5 µg/mL. The effect of each compound was expressed as percentage inhibition agonist-induced platelet aggregation compared with vehicle treatment. Data are presented as the mean±S.E.M. for six experiments. The $IC_{50}$ value was obtained by linear regression, and is expressed as the compound concentration required to produce 50% inhibition of agonist-induced platelet aggregation in comparison to vehicle treatment.

(ii) Test Result

| Compound (Example No.) | IC$_{50}$ ($\mu$M) |
|---|---|
| 1-(2) | <0.02 |
| 5-(4) | <0.02 |
| 15-(4) | <0.02 |
| 19 | <0.02 |
| 25 | <0.02 |

It appeared, from the above-mentioned Test Result, that the compound (I) or pharmaceutically acceptable salts thereof of the present invention have an inhibiting activity against platelet aggregation. Therefore, the compound (I) or pharmaceutically acceptable salts thereof are useful for preventing or treating disorders induced by platelet aggregation, such as thrombosis.

Additionally, it was further confirmed that the compounds (I) of the present invention lack undesired side-effects of non-selective NSAIDs, such as gastrointestinal disorders, bleeding, renal toxicity, cardiovascular affection, etc.

The object compound (I) or pharmaceutically acceptable salts thereof of this invention possesses COX inhibiting activity and possesses strong anti-inflammatory, antipyretic, analgesic, antithrombotic, anti-cancer activities, and so on.

The object compound (I) and pharmaceutically acceptable salt thereof, therefore, are useful for treating and/or preventing COX mediated diseases, inflammatory conditions, various pains, collagen diseases, autoimmune diseases, various immunological diseases, thrombosis, cancer and neurodegenerative diseases in human beings or animals by using administered systemically or topically.

More particularly, the object compound (I) and pharmaceutically acceptable salts thereof are useful for treating and/or preventing inflammation and acute or chronic pain in joint and muscle [e.g. rheumatoid arthritis, rheumatoid spondylitis, osteoarthritis, gouty arthritis, juvenile arthritis, scapulohumeral periarthritis, cervical syndrome, etc.]; lumbago;

inflammatory skin condition [e.g. sunburn, burns, eczema, dermatitis, etc.];

inflammatory eye condition [e.g. conjunctivitis, etc.];

lung disorder in which inflammation is involved [e.g. asthma, bronchitis, pigeon fancier's disease, farmer's lung, etc.]; condition of the gastrointestinal tract associated with inflammation [e.g. aphthous ulcer, Chrohn's disease, atopic gastritis, gastritis varialoforme, ulcerative colitis, coeliac disease, regional ileitis, irritable bowel syndrome, etc.]; gingivitis; menorrhalgia; inflammation, pain and tumescence after operation or injury [pain after odontectomy, etc.];

pyrexia, pain and other conditions associated with inflammation, particularly those in which lipoxygenase and cyclooxygenase products are a factor, systemic lupus erythematosus, scleroderma, polymyositis, tendinitis, bursitis, periarteritis nodose, rheumatic fever, Sjogren's syndrome, Behcet disease, thyroiditis, type I diabetes, nephrotic syndrome, aplastic anemia, myasthenia gravis, uveitis contact dermatitis, psoriasis, Kawasaki disease, sarcoidosis, Hodgkin's disease, Alzheimers disease, or the like.

Additionally, the object compound (I) or a salt thereof is expected to be useful as therapeutical and/or preventive agents for cardiovascular or cerebrovascular diseases, the diseases caused by hyperglycemia and hyperlipemia.

The object compound (I) and a salt thereof can be used for prophylactic and therapeutic treatment of arterial thrombosis, arterial sclerosis, ischemic heart diseases [e.g. angina pectoris (e.g. stable angina pectoris, unstable angina pectoris including imminent infarction, etc.), myocardial infarction (e.g. acute myocardial infarction, etc.), coronary thrombosis, etc.], ischemic brain diseases [e.g. cerebral infarction (e.g. acute cerebral thrombosis, etc.), cerebral thrombosis (e.g. cerebral embolism, etc.), transient cerebral ischemia (e.g. transient ischemic attack, etc.), cerebrovascular spasm after cerebral hemorrhage (e.g. cerebrovascular spasm after subarachnoid hemorrhage, etc.), etc.], pulmonary vascular diseases (e.g. pulmonary thrombosis, pulmonary embolism etc.), peripheral circulatory disorder [e.g. arteriosclerosis obliterans, thromboangiitis obliterans (i.e. Buerger's disease), Raynaud's disease, complication of diabetes mellitus (e.g. diabetic angiopathy, diabetic neuropathy, etc.), phiebothrombosis (e.g. deep vein thrombosis, etc.), etc.], complication of tumors (e.g. compression thrombosis), abortion [e.g. placental thrombosis, etc.], restenosis and reocclusion [e.g. restenosis and/or reocclusion after percutaneous transluminal coronary angioplasty (PTCA), restenosis and reocclusion after the administration of thrombolytic drug (e.g. tissue plasminogen activator (TPA), etc.)], thrombus formation in case of vascular surgery, valve replacement, extracorporeal circulation [e.g. surgery (e.g. open heart surgery, pump-oxygenator, etc.) hemodialysis, etc.] or transplantation, disseminated intravascular coagulation (DIC), thrombotic thrombocytopenia, essential thrombocytosis, inflammation (e.g. nephritis, etc.), immune diseases, atrophic thrombosis, creeping thrombosis, dilation thrombosis, jumping thrombosis, mural thrombosis, etc.

The object compound (I) and a salt thereof can be used for the adjuvant therapy with thrombolytic drug (e.g. TPA, etc.) or anticoagulant (e.g. heparin, etc.).

And, the compound (I) is also useful for inhibition of thrombosis during extra corporeal circulation such as dialysis.

Particularly, the following diseases are exemplified:

pains caused by or associated with rheumatoid arthritis, osteoarthritis, lumbar rheumatism, rheumatoid spondylitis, gouty arthritis, juvenile arthritis, etc; lumbago;

cervico-omo-brachial syndrome; scapulohumeral periarthritis; pain and tumescence after operation or injury; etc.

For therapeutic purpose, the compound (I) and a pharmaceutically acceptable salt thereof of the present invention can be used in a form of pharmaceutical preparation containing one of said compounds as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, inhalant, suppositories, solution, lotion, suspension, emulsion, ointment, gel, or the like. If desired, there may be included in these preparations, auxiliary substances, stabilizing agents, wetting, or emulsifying agents, buffers and other commonly used additives.

While the dosage of therapeutically effective amount of the compound (I) will vary depending upon the age and condition of each individual patient, an average single dose of about 0.01 mg, 0.1 mg, 1 mg, 10 mg, 50 mg, 100 mg, 250 mg, 500 mg and 1000 mg of the compound (I) may be effective for treating the above-mentioned diseases. In general, amounts between 0.01 mg/body and about 1,000 mg/body may be administered per day.

For therapeutic purpose, the analgesic agent of the present invention can be used in a form of pharmaceutical preparation suitable for oral, parenteral or external administration. The pharmaceutical preparations may be capsules, tablets, dragees, granules, inhalant, suppositories, solution, lotion, suspension, emulsion, ointment, gel, or the like.

Particularly, the analgesic agent of this invention is useful for treating or preventing acute or chronic pains associated with acute or chronic inflammations in human beings or animals by using administered systemically or topically.

The patents, patent applications and publications cited herein are incorporated by reference.

The following Examples are given for the purpose of illustrating the present invention in detail.

EXAMPLE 1

(1) To a solution of trifluoroacetoamidine (4.24 g, 37.8 mmol) in methanol (20 mL), were added 4-methoxyphenylhydrazine hydrochloride (4.72 g, 27 mmol) and then triethylamine (3.77 mL, 27 mmol) at room temperature. The mixture was stirred for 6 hours. The solvent was removed under reduced pressure. 20 mL of water and 50 mL of ethyl acetate-tetrahydrofuran (9:1) were added to the residue and the organic layer was separated and the aqueous layer was extracted with 50 mL of ethyl acetate-tetrahydrofuran (9:1). A combined organic layer was washed with water and brine, and dried over magnesium sulfate. The solvent was removed under reduced pressure to give 2,2,2-trifluoro-N'-(4-methoxyphenyl)ethanehydrazonamide (6.82 g, 108.2% yield). The residue was used for the next reaction without purification.

(2) To a solution of 2,2,2-trifluoro-N'-(4-methoxyphenyl)ethanehydrazonamide (0.92 g, 3.95 mmol) in 10 mL of dioxane, were added pyridine (0.319 mL, 3.95 mmol) and a solution of 4-methoxybenzoyl chloride (673 mg, 3.95 mmol) in 3 mL of dioxane. The mixture was refluxed with stirring for 12 hours. The solvent was removed under reduced pressure. 50 mL of dichloromethane and 20 mL of 0.1 N hydrochloric acid were added to the residue and the organic layer was separated. The aqueous layer was extracted with 50 mL of dichloromethane. A combined organic layer was washed with 0.1 N hydrochloric acid and brine and dried over magnesium sulfate. The solvent was removed under reduced pressure. The residue was purified by silica gel column chromatography (toluene-ethyl acetate 9:1) and then recrystallized with diisopropyl ether-hexane to give pale brown needle of 1,5-bis(4-methoxyphenyl)-3-(trifluoromethyl)-1H-1,2,4-triazole (0.67 g, 48.6% yield).

1H NMR (DMSO-d6, ppm) δ 7.45 (t, J=8.9 Hz, 4H), 7.09 (d, J=8.9 Hz, 2H), 6.98 (d, J=8.9 Hz, 2H), 3.83 (s, 3H), 3.78 (s, 3H).

MS (ESI, m/e) 350 (M+1).

EXAMPLE 2

To a suspension of 6-methylnicotinoic acid (329 mg, 2.4 mmol) in dichloromethane (3 mL), was added oxalyl chloride (0.209 mL, 2.4 mmol). And then 10 micro-L of dimethylformamide was added to the mixture. The mixture was stirred for 1 hour and the solvent was removed under reduced pressure. The residue was azeotroped with dichloromethane. To the residue, was added 3 mL of dioxane. Then a solution of 2,2,2-trifluoro-N'-(4-methoxyphenyl)ethanehydrazonamide (466 mg, 2 mmol) and diisopropylethylamine (0.418 mL, 2.4 mmol) in 4.5 mL of dioxane was added to the mixture and the mixture was refluxed with stirring for 3.5 hours. The solvent was removed under reduced pressure, and dichloromethane and 0.1 N hydrochloric acid were added to the residue. The organic layer was separated, washed with 0.1 N hydrochloric acid, water, and brine, dried over magnesium sulfate. The crude product was purified by silica gel column chromatography (8:1 toluene-ethyl acetate). The desired product was rinsed with hexane and dried in vacuo to give 5-[1-(4-methoxyphenyl)-3-(trifluoromethyl)-1H-1,2,4-triazol-5-yl]2-methylpyridine (102 mg, 14.8% yield).

1H NMR (DMSO-d6, ppm) δ 8.51 (d, J=2.2 Hz, 1H), 7.74 (dd, J=2.2, 8.2 Hz, 1H), 7.50 (d, J=8.8 Hz, 2H), 7.34 (d, J=8.2 Hz, 1H), 7.09 (d, J=8.8 Hz, 2H), 3.83 (s, 3H), 3.32 (s, 3H).

MS (ESI, m/e) 335 (M+1).

EXAMPLE 3

To a suspension of 4-cyanobenzoic acid (353 mg, 2.4 mmol) in dichloromethane (3 mL), was added oxalyl chloride (0.209 mL, 2.4 mmol). And then 10 micro-L of dimethylformamide was added to the mixture. The mixture was stirred for 1 hour and the solvent was removed under reduced pressure. The residue was azeotroped with dichloromethane. To the residue, was added 3 mL of dioxane. Then a solution of 2,2,2-trifluoro-N'-(4-methoxyphenyl)ethanehydrazonamide (466 mg, 2 mmol) and diisopropylethylamine (0.418 mL, 2.4 mmol) in 4.5 mL of dioxane was added to the mixture and the mixture was refluxed with stirring for 3.5 hours. The solvent was removed under reduced pressure, and dichloromethane and 0.1 N hydrochloric acid were added to the residue. The organic layer was separated, washed with 0.1 N hydrochloric acid, water, and brine, dried over magnesium sulfate. The crude product was purified by silica gel column chromatography (20:1–10:1 toluene-ethyl acetate). The desired product was rinsed with diisopropyl ether and dried in vacuo to give 4-[1-(4-methoxyphenyl)-3-(trifluoromethyl)-1H-1,2,4-triazol-5-yl]benzonitrile (88 mg, 12.8% yield).

1H NMR (DMSO-d6, ppm) δ 7.94 (d, J=8.5 Hz, 2H), 7.67 (d, J=8.5 Hz, 2H), 7.50 (d, J=9.0 Hz, 2H), 7.09 (d, J=9.0 Hz, 2H), 3.83 (s, 3H).

EXAMPLE 4

A mixture of 2,2,2-trifluoro-N'-(4-methoxyphenyl)ethanehydrazonamide (350 mg, 1.5 mmol), 4-methylbenzoyl chloride (0.238 mL, 1.8 mmol), and diisopropylethylamine (0.314 mL, 1.8 mmol) in dioxane (3.5 mL) was refluxed with stirring for 13 hours. After cooling, the solvent was removed under reduced pressure. Dichloromethane and 0.1 N hydrochloric acid were added to the residue, and the organic layer was separated, washed with 0.1 N hydrochloric acid, sat. sodium bicarbonate, and brine, and dried over magnesium sulfate. The solvent was removed under reduced pressure. The residue was purified by silica gel column chromatography (hexane-ethyl acetate 9:1). The desired product was isolated by filtration, washed with hexane, and dried in vacuo to give 1-(4-methoxyphenyl)-5-(4-methylphenyl)-3-(trifluoromethyl)-1H-1,2,4-triazole (194 mg, 38.8% yield).

1H NMR (DMSO-d6, ppm) δ 7.46 (d, J=6.8 Hz, 2H), 7.38 (d, J=8.1 Hz, 2H), 7.24 (d, J=8.1 Hz, 2H), 7.08 (d, J=6.8 Hz, 2H), 3.82 (s, 3H), 2.31 (s, 3H).

MS (ESI, m/e) 334 (M+1).

EXAMPLE 5

(1) Under ice-bath cooling, potassium cyanate (1.71 g, 21.1 mmol) was added to a suspension of 4-methoxyphenylhydrazine hydrochloride (3.35 g, 19.2 mmol) in water (40 mL). The mixture was stirred for 1 hour at the same temperature. And then the mixture was warmed to room temperature and stirred for 12 hours. An insoluble material was isolated by filtration, washed with water, and dried in vacuo to give 2-(4-methoxyphenyl) hydrazinecarboxamide (2.45 g, 70.5% yield).

1H NMR (DMSO-d6, ppm) δ 7.64 (s, 1H), 7.26 (s, 1H), 6.78 (d, J=8.8 Hz, 2H), 6.67 (d, J=8.8 Hz, 2H), 5.90 (s, 2H), 3.66 (s, 3H).

MS (ESI, m/e) 223 (M+1+MeCN).

(2) To a suspension of 2-(4-methoxyphenyl) hydrazinecarboxamide (1.81 g, 9.99 mmol) in 20 mL of toluene, pyridine (1.01 mL, 12.5 mmol) and then a solution of 4-methoxybenzoyl chloride (2.13 g, 12.5 mmol) in 10 mL of toluene were added. The mixture was refluxed with stirring for 1 hour. After cooling, 500 mL of ethyl acetate-tetrahydrofuran (9:1) and 100 mL of water were added to the mixture. After vigorous shaking, an insoluble material was isolated by filtration and dired in vacuo to give 2-(4-methoxybenzoyl)-2-(4-methoxyphenyl) hydrazinecarboxamide (1.95 g, 61.9% yield).

1H NMR (DMSO-d6, ppm) δ 8.86 (br s, 1H), 7.49 (br d, J=7.4 Hz, 2H), 7.28 (br s, 2H), 6.89 (m, 4H), 3.77 (s, 3H), 3.73 (s, 3H).

MS (ESI, m/e) 316 (M+1).

(3) A mixture of 2-(4-methoxybenzoyl)-2-(4-methoxyphenyl)hydrazinecarboxamide (1.9 g, 6.03 mmol) in 10% potassium hydroxide solution (16 mL)-ethanol (8 mL) was heated at 60° C. for 1.5 hours. After cooling, the solvent was removed under reduced pressure. Water was added to the residue and the mixture was adjusted pH to ca. 2. A generated precipitate was isolated by filtration, washed with water, and dried in vacuo to give 1,5-bis(4-methoxyphenyl)-1H-1,2,4-triazol-3-ol (1.51 g, 84.3% yield).

1H NMR (DMSO-d6, ppm) δ 7.32 (d, J=8.9 Hz, 2H), 7.28 (d, J=8.9 Hz, 2H), 7.01 (d, J=8.9 Hz, 2H), 6.93 (d, J=8.9 Hz, 2H), 3.80 (s, 3H), 3.77 (s, 3H).

MS (ESI, m/e) 298 (M+1).

(4) A mixture of 1,5-bis (4-methoxyphenyl)-1H-1,2,4-triazol-3-ol (1.5 g, 5.05 mmol), potassium carbonate (2.09 g, 15.1 mmol), and iodomethane (3.14 mL, 50.5 mmol) in dimethylformamide (15 mL) was stirred overnight. 100 mL of water and 300 mL of ethyl acetate-tetrahydrofuran (9:1) were poured into the mixture and the organic layer was separated, washed with brine-water (1:1) and brine, and dried over magnesium sulfate. The solvent was removed under reduced pressure. The residue was purified by column chromatography (hexane-ethyl acetate 4:1–2:3). 3-Methoxy-1,5-bis(4-methoxyphenyl)-1H-1,2,4-triazole was recrystallized from ethyl acetate-hexane. (658 mg, 41.9% yield)

1H NMR (DMSO-d6, ppm) δ 7.34 (d, J=8.9 Hz, 2H), 7.32 (d, J=8.9 Hz, 2H), 7.03 (d, J=8.9 Hz, 2H), 6.94 (d, J=8.9 Hz, 2H), 3.93 (s, 3H), 3.80 (s, 3H), 3.76 (s, 3H).

MS (ESI, m/e) 312 (M+1).

mp 125.6–126.0° C.

EXAMPLE 6

(1) A mixture of 4-methoxyphenylhydrazine hydrochloride (2.76 g, 15.8 mmol) and potassium cyanate (1.94 g, 20 mmol) in ethanol (30 mL) was refluxed for 10 hours. After cooling, a generated precipitate was isolated by filtration, washed with EtOH, and dried to give 2-(4-methoxyphenyl) hydrazinecarbothioamide (2.46 g, 78.9% yield).

1H NMR (DMSO-d6, ppm) δ 9.21 (s, 1H), 7.73 (br s, 1H), 7.62 (s, 1H), 7.42 (br s, 1H), 6.81 (d, J=9.0 Hz, 2H), 6.62 (d, J=9.0 Hz), 3.67 (s, 3H).

(2) A mixture of 2-(4-methoxyphenyl) hydrazinecarbothioamide (0.5 g, 2.53 mmol), 4-methoxybenzoyl chloride (541 mg, 3.17 mmol), and pyridine (0.256 mL, 3.17 mmol) intoluene (10 mL) was refluxed for 1 hour. After cooling, the solvent was removed under reduced pressure. diisopropyl ether and small amount of methanol was added to the residue and a generated precipitate was isolated by filtration, washed with methanol-diisopropyl ether, and dried in vacuo to give 2-(4-methoxybenzoyl)-2-(4-methoxyphenyl) hydrazinecarbothioamide (277 mg, 33% yield).

1H NMR (DMSO-d6, ppm) δ 10.27 (s, 1H), 8.21 (br s, 1H), 7.96 (br s, 1H), 7.52 (d, J=8.6 Hz, 2H), 7.40 (d, J=8.8 Hz, 2H), 6.91 (br d, J=8.6 Hz), 3.78 (s, 3H), 3.74 (s, 3H).

MS (ESI, m/e) 332 (M+1).

(3) A mixture of 2-(4-methoxybenzoyl)-2-(4-methoxyphenyl)hydrazinecarbothioamide (200 mg, 0.604 mmol) in 10% potassium hydroxide solution (2 mL)-ethanol (1 mL) was refluxed for 4 hours. After cooling, the mixture was adjusted pH to ca. 2 and a generated precipitate was isolated by filtration, washed with water, and dried in vacuo to give 1,5-bis(4-methoxyphenyl)-1H-1,2,4-triazole-3-thiol (52 mg, 27.5% yield).

1H NMR (DMSO-d6, ppm) δ 7.39 (d, J=8.7 Hz, 2H), 7.36 (d, J=8.5 Hz, 2H), 7.04 (d, J=8.7 Hz, 2H), 7.00 (d, J=8.5 Hz, 2H), 3.80 (s, 3H), 3.78 (s, 3H).

MS (ESI, m/e) 314 (M+1).

(4) To a mixture of 1,5-bis(4-methoxyphenyl)-1H-1,2,4-triazole-3-thiol (470 mg, 1.5 mmol) in 1N sodium hydroxide solution (5 mL), was added iodomethane (0.934 mL, 15 mmol). The mixture was shaken overnight. Dichloromethane and water were added to the mixture and the organic layer was separated, washed with 0.1 N hydrochloric acid and sat sodium bicarbonate, and brine, and dried over magnesium sulfate. The solvent was removed under reduced pressure.The generated precipitate was isolated by filtration, washed with diisopropyl ether, and dried in vacuo to give 1,5-bis(4-methoxyphenyl)-3-(methylthio)-1H-1,2,4-triazole (235 mg, 47.9% yield).

1H NMR (DMSO-d6, ppm) δ 7.36 (d, J=8.9 Hz, 2H), 7.34 (d, J=8.9 Hz, 2H), 7.04 (d, J=8.9 Hz, 2H), 6.94 (d, J=8.9 Hz, 2H), 3.81 (s, 3H), 3.76 (s, 3H), 2.58 (s, 3H).

MS (ESI, m/e) 328 (M+1).

(5) A mixture of 1,5-bis(4-methoxyphenyl)-3-(methylthio)-1H-1,2,4-triazole (150 mg, 0.458 mmol) and m-chloroperbenzoic acid (119 mg, 0.687 mmol) in dichloromethane (1.5 mL) was stirred for 3 hours at room temperature. The solvent was removed under reduced pressure. The residue was purified by silica gel column chromatography (dichloromethane-2% methanol in dichloromethane) to give 1,5-bis(4-methoxyphenyl)-3-(methylsulfinyl)-1H-1,2,4-triazole (152 mg, 96.6% yield).

MS (ESI, m/e) 344 (M+1).

(6) A mixture of 1,5-bis(4-methoxyphenyl)-3-(methylsulfinyl)-1H-1,2,4-triazole (152 mg, 0.443 mmol) and m-chloroperbenzoic acid (115 mg, 0.664 mmol) in dichloromethane (1.5 mL) was stirred at room temperature for 6 hours. Dichloromethane and sat. sodium bicarbonate solution were poured into the mixture and the organic layer was separated. The aqueous layer was extracted with dichloromethane. A combined organic layer was washed with sat. sodium bicarbonate solution and brine and dried over magnesium sulfate. The solvent was removed under reduced pressure. The residue was triturated with diisopropyl ether and the precipitate was isolated by filtration, washed with diisopropyl ether, and dried in vacuo to give 1,5-bis(4-methoxyphenyl)-3-(methylsulfonyl)-1H-1,2,4-triazole (130 mg, 81.7% yield).

1H NMR (DMSO-d6, ppm) δ 7.46 (d, J=8.9 Hz, 7.42 (d, J=8.9 Hz, 2H), 7.10 (d, J=8.9 Hz, 2H), 6.99 (d, J=8.9 Hz, 2H), 3.83 (s, 3H), 3.78 (s, 3H), 3.44 (s, 3H).

MS (ESI, m/e) 360 (M+1).

EXAMPLE 7

To a suspension of 4-(1H-pyrrol-1yl)benzoic acid (337 mg, 1.8 mmol) in dichloromethane (3.5 mL), oxalyl chloride (0.157 mL, 1.8 mmol) and then dimethylformamide (10 microL) were added. The mixture was stirred overnight. The solvent was removed under reduced pressure. Pyridine (0.146 mL, 1.8 mmol) and a solution of 2,2,2-trifluoro-N'-(4-methoxyphenyl)ethanehydrazonamide (350 mg, 1.5 mmol) in 3.5 mL of dioxane were added to a suspension of the acyl chloride in 3.5 mL of dioxane. The mixture was refluxed with stirring for 3 hours. After cooling, the solvent was removed under reduced pressure and 0.1 N hydrochloric acid and dichloromethane were added to the residue. The organic layer was separated and the aqueous layer was extracted with dichloromethane. A combined layer was washed with 0.1 N hydrochloric acid and brine, and dried over magnesium sulfate. The solvent was removed under reduced pressure. The desired product was purified by silica gel column chromatography (hexane-ethyl acetate 8:1–5:1) to give 1-(4-methoxyphenyl)-5-[4-(1H-pyrrol-1yl)phenyl]-3-(trifluoromethyl)-1H-1,2,4-triazole (74 mg, 12.8% yield)

1H NMR (DMSO-d6, ppm) δ 7.69 (d, J=8.9 Hz, 2H), 7.54 (d, J=8.9 Hz, 2H), 7.52 (d, J=8.9 Hz, 2H), 7.46 (d, 4.4 Hz, 2H), 7.11 (d, J=8.9 Hz, 2H), 6.29 (d, J=4.4 Hz, 2H), 3.83 (s, 3H).

MS (ESI, m/e) 385 (M+1).

EXAMPLE 8

Under ice-cooling, oxalyl chloride (0.206 mL, 2.4 mmol) and then cat. dimethylformamide were added to a suspension of 6-methoxynicotinic acid (367 mg, 2.4 mmol) in 3 mL of dichloromethane. The mixture was stirred at room temperature for 1.5 hour. The solvent was removed under reduced pressure and the residue was azeotropped with dioxane. A solution of 2,2,2-trifluoro-N'-(4-methoxyphenyl)ethanehydrazonamide (466 mg, 2.0 mmol) and pyridine (0.194 mL, 2.4 mmol) in 5 mL of dioxane was added to a suspension of the residue in 1 mL of dioxane. The mixture was refluxed with stirring for 4 hours. After cooling, the solvent was removed under reduced pressure. The desired product was purified by silica gal column chromatogaraphy (hexane-ethyl acetate 4:1) to give 2-methoxy-5-[1-(4-methoxyphenyl)-3-(trifluoromethyl)-1H-1,2,4-triazol-5-yl] pyridine (90 mg, 14.9% yield).

1H NMR (DMSO-d6, ppm) δ 8.26 (d, J=2.4 Hz, 1H), 7.76 (dd, J=2.4, 8.7 Hz, 1H), 7.51 (d, J=8.9 Hz, 2H), 7.10 (d, J=8.9 Hz, 2H), 6.89 (d, J=8.7 Hz, 1H), 3.87 (s, 3H), 3.83 (s, 3H).

MS (ESI, m/e) 351 (M+1).

EXAMPLE 9

(1) Triethylamine (1.54 mL, 11 mmol) and then 4-cyanophenylhydrazine hydrochloride (1.71 g, 10 mmol) were added to a solution of trifluoroacetoamidine (1.57 g, 14 mmol) in methanol (10 mL). The mixture was stirred overnight. The solvent was removed under reduced pressure. 20 mL of water and 50 mL of ethyl acetate-tetrahydrofuran (9:1) were added to the residue and the organic layer was separated and the aqueous layer was extracted with 50 mL of ethyl acetate-tetrahydrofuran (9:1). A combined organic layer was washed with water and brine, and dried over magnesium sulfate. The solvent was removed under reduced pressure. The residue was isolated by filtartion, washed with diisopropyl ether-hexane, and dried in vacuo to give 2,2,2-trifluoro-N'-(4-cyanophenyl)ethanehydrazonamide (2.07 g, 90.5% yield).

1H NMR (DMSO-d6, ppm) δ 9.23 (s, 1H), 7.58 (d, J=8.8 Hz, 2H), 6.99 (d, J=8.9 Hz, 2H), 6.72 (s, 1H).

(2) A mixture of 2,2,2-trifluoro-N'-(4-cyanophenyl) ethanehydrazonamide (456 mg, 2.0 mmol), 4-methylbenzoyl chloride (406 mg, 2.4 mmol), 4-dimethylaminopyridine (293 mg, 2.4 mmol), and pyridine (0.194 mL, 2.4 mmol) in dioxane (5.5 mL) was refluxed with stirring overnight. After cooling, the solvent was removed under reduced pressure. Dichloromethane and 0.1 N hydrochloric acid were added to the residue, and the organic layer was separated, washed with 0.1 N hydrochloric acid, sat. sodium bicarbonate, and brine, and dried over magnesium sulfate. The solvent was removed under reduced pressure. The residue was purified by silica gel column chromatography. The desired product was isolated by filtration, washed with hexane, and dried in vacuo to give 4-[5-(4-methoxyphenyl)-3-(trifluoromethyl)-1H-1,2,4-triazol-1-yl] benzonitrile (138 mg, 20.1% yield).

1H NMR (DMSO-d6, ppm) δ 8.06 (d, J=8.7 Hz, 2H), 7.74 (d, J=8.7 Hz, 2H), 7.43 (d, J=8.9 Hz, 2H), 7.01 (d, J=8.9 Hz, 2H), 3.79 (s, 3H).

MS (ESI, m/e) 345 (M+1).

EXAMPLE 10

A mixture of 1,5-bis(4-methoxyphenyl)-1H-1,2,4-triazol-3-ol (0.3 g, 1.01 mmol), potassium carbonate (418 mg, 3.01 mmol), and iodoethane (0.406 mL, 5.05 mmol) in dimethylformamide (3 mL) was stirred for 3 days. Water and ethyl acetate-tetrahydrofuran (9:1) were poured into the mixture and the organic layer was separated, washed with brine-water (1:1) and brine, and dried over magnesium sulfate. The solvent was removed under reduced pressure. The residue was purified by column chromatography to give 3-ethoxy-1,5-bis(4-methoxyphenyl)-1H-1,2,4-triazole (143 mg, 43.6% yield).

1H NMR (DMSO-d6, ppm) δ 7.35 (d, J=8.9 Hz, 2H), 7.28 (d, 8.9 Hz, 2H), 7.02 (d, J=8.9 Hz, 2H), 6.93 (d, J=8.9 Hz, 2H), 4.29 (q, J=7.0 Hz, 2H), 3.80 (s, 3H), 3.76 (s, 3H), 1.35 (t, J=7.0 Hz, 3H).

MS (ESI, m/e) 326 (M+1).

EXAMPLE 11

(1) Triethylamine (0.439 mL, 3.15 mmol) and then 4-methylphenylhydrazine hydrochloride (500 mg, 3.15 mmol) were added to a solution of trifluoroacetoamidine (494 mg, 4.41 mmol) in methanol (2 mL). The mixture was stirred overnight. The solvent was removed under reduced pressure. 20 mL of 1 N hydrochloric acid and 50 mL of ethyl acetate-tetrahydrofuran (9:1) were added to the residue and the organic layer was separated. The organic layer was washed with water and brine, and dried over magnesium sulfate. The solvent was removed under reduced pressure. 2,2,2-Trifluoro-N'-(4-methylphenyl)ethanehydrazonamide was used for the next reaction without purification (0.62 g, 90.6% yield).

(2) A mixture of 2,2,2-trifluoro-N'-(4-methylphenyl) ethanehydrazonamide (0.62 g, 2.85 mmol), 4-methoxybenzoyl chloride (584 mg, 3.43 mmol), and pyridine (0.277 mL, 3.43 mmol) in dioxane (6 mL) was refluxed with stirring for 1 hour. After cooling, the solvent was removed under reduced pressure. ethyl acetate-tetrahydrofuran (9:1) and water was poured into the residue and the organic layer was separated, washed with 0.1 N hydrochloric acid, water, and brine, and dried over magnesium sulfate. The solvent was removed under reduced pressure and the residue was purified by column chromatography (hexane-ethyl acetate 8:1–1:1). The desired product was recrystallized from hexane and dried in vacuo to give 5-(4-methoxyphenyl)-1-(4-methylphenyl)-3-(trifluoromethyl)-1H-1,2,4-triazole (370 mg, 38.9% yield).

1H NMR (DMSO-d6, ppm) δ 7.3–7.5 (m, 6H), 6.98 (d, J=8.9 Hz, 2H), 3.77 (s, 3H), 2.39 (s, 3H)

MS (ESI, m/e) 334 (M+1)

EXAMPLE 12

(1) Triethylamine (2.24 mL, 16.1 mmol) and then 5-hydrazino-2-methoxypyridine dihydrochloride (1.7 g, 8.03 mmol) were added to a solution of trifluoroacetoamidine (0.3 g, 2.68 mmol) in methanol (3 mL). The mixture was stirred overnight. The solvent was removed under reduced pressure. 20 mL of 1 N hydrochloric acid and 50 mL of ethyl acetate-tetrahydrofuran (9:1) were added to the residue and the organic layer was separated. The organic layer was washed with water and brine, and dried over magnesium sulfate. The solvent was removed under reduced pressure. The obtained 2,2,2-trifluoro-N'-(6-methoxypyridin-3-yl)ethanehydrazonamide was used for the next reaction without purification (0.37 g, 59% yield).

MS (ESI, m/e) 235 (M+1).

(2) A mixture of 2,2,2-trifluoro-N'-(6-methoxypyridin-3-yl)ethanehydrazonamide (0.2 g, 0.854 mmol), 4-methoxybenzoyl chloride (175 mg, 1.02 mmol), pyridine (0.083 mL, 1.02 mmol), and 4-dimethylaminopyridine (125 mg, 1.02 mmol) in dioxane (2 mL) was refluxed with stirring overnight. After cooling, the solvent was removed under reduced pressure. ethyl acetate-tetrahydrofuran (9:1) and water was poured into the residue and the organic layer was separated, washed with 0.1 N hydrochloric acid, water, and brine, and dried over magnesium sulfate. The solvent was removed under reduced pressure and the residue was purified by column chromatography to give 2-methoxy-5-[5-(4-methoxyphenyl)-3-(trifluoromethyl)-1H-1,2,4-triazol-1-yl] pyridine (57 mg, 19.1% yield).

1H NMR (DMSO-d6, ppm) δ 8.38 (d, J=2.7 Hz, 1H), 7.94(dd, J=2.7, 8.8 Hz, 1H), 7.46 (d, J=8.9 Hz, 2H), 6.95–7.05 (m, 3H), 3.92 (s, 3H), 3.79 (s, 3H).

MS (ESI, m/e) 351 (M+1).

EXAMPLE 13

Potassium carbonate (697 mg, 5.05 mmol) was added to a solution of 1,5-bis(4-methoxyphenyl)-1H-1,2,4-triazol-3-ol (0.3 g, 1.01 mmol) in dimethylformamide (3 mL). After 10 minute stirring, 2,2,2-trifluoroethyl iodide (0.497 mL, 5.05 mmol) was added to the mixture and the mixture was heated at 100° C. for 3 hours. After cooling, 100 mL of ethyl acetate and 20 mL of water were poured into the mixture. The organic layer was separated, washed with water and brine, and dried over magnesium sulfate. The solvent was removed under reduced pressure. The residue was purified by silica gel column chromatography (hexane-ethyl acetate 10:1–5:1). The desired product was triturated with hexane, isolated by filtartion, and dried in vacuo to give 1,5-bis(4-methoxyphenyl)-3-(2,2,2-trifluoroethoxy)-1H-1,2,4-triazole (205 mg, 53.6%).

1H NMR (DMSO-d6, ppm) δ 7.36 (d, J=8.8 Hz, 2H), 7.33 (d, J=8.8 Hz, 2H), 7.04 (d, J=8.8 Hz, 2H), 6.95 (d, J=8.8 Hz, 2H), 4.99 (q, J=8.8 Hz, 2H), 3.81 (s, 3H), 3.76 (s, 3H).

MS (ESI, m/e) 380 (M+1).

EXAMPLE 14

(1) To a suspension of 2-(4-methoxyphenyl) hydrazinecarboxamide (1.18 g, 6.53 mmol) in 10 mL of toluene, pyridine (0.69 mL, 8.57 mmol) and then a solution of 6-methoxynicotinoyl chloride (1.4 g, 8.16 mmol) in 5 mL of toluene were added. The mixture was refluxed with stirring for 1 hour.

After cooling at 80° C., 10 mL of water was added to the mixture. After vigorous shaking, an insoluble material was isolated by filtration and washed with water and toluene then dried in vacuo to give 2-(4-methoxyphenyl)-2-((6-methoxypyridin-3-yl)carbonyl) hydrazinecarboxamide (560 mg, 21.7% yield).

1H NMR (DMSO-d6, ppm) δ 3.75 (3H, s), 3.87 (3H, s), 6.14 (2H, br s), 6.78–6.87 (1H, m), 6.87–7.00 (2H, m), 7.12–7.35 (2H, m), 7.78–7.92 (1H, m), 8.37 (1H, br s), 8.98 (1H, br s), MS (ESI, m/e) 339 (M+Na).

(2) A mixture of 2-(4-methoxyphenyl)-2-((6-methoxypyridin-3-yl)carbonyl)hydrazine carboxamide (550 mg, 1.74 mmol) in 10% sodium hydroxide solution (4 mL)-ethanol (2 mL) was heated at 60° C. for 1 hour. After cooling, the solvent was removed under reduced pressure. 2N-HCl was added to the residue and the mixture was adjusted pH to ca. 4. A generated precipitate was isolated by filtration, washed with water, dried in vacuo to give 1-(4-methoxyphenyl)-5-(6-methoxypridin-3-yl)-1H-1,2,4-triazol-3-ol (280 mg, 54% yield).

1H NMR (DMSO-d6, ppm) δ 3.80 (3H, s), 3.85 (3H, s), 6.80–6.90 (1H, m), 6.97–7.12 (2H, m), 7.28–7.42 (2H, m), 7.58–7.70 (1H, m), 8.18–8.27 (1H, m), 11.38 (1H, br s), MS (ESI, m/e) 299 (M+1).

(3) A mixture of 1-(4-methoxyphenyl)-5-(6-methoxypridin-3-yl)-1H-1,2,4-triazol-3-ol (200 mg, 0.67 mmol), potassium carbonate (278 mg, 2.01 mmol), and 2-iodo-1,1,1-trifluoroethane (0.198 mL, 2.01 mmol) in dimethylsulfoxide (1 mL) were heated at 100° C. for 1 hour. After cooling, ice water and ethyl acetate were poured into the mixture and the organic layer was separated, washed with brine, and dried over magnesium sulfate. The solvent was removed under reduced pressure. The residue was purified by column chromatography (toluene-ethyl acetate 10:1). The desired product was washed with hexane to give 2-methoxy-5-(1-(4-methoxyphenyl)-3-(2,2,2-trifluoroethoxy)-1H-1,2,4-triazole-5-yl)pyridine. (60 mg, 23.5% yield)

1H NMR (CDCl3, ppm) δ 3.86 (3H, s), 3.93 (3H, s), 4.65–4.85 (2H, m), 6.71 (1H, d, J=8.4 Hz), 6.89–7.05 (2H, m), 7.20–7.38 (2H, m), 7.71 (1H, dd, J=2.5, 8.7 Hz), 8.26 (1H, d, J=2.4 Hz), MS (ESI, m/e) 381 (M+1).

mp 82–83° C.

EXAMPLE 15

(1) Potassium cyanate (8.41 g, 104 mmol) was added to a solution of 5-hydrazino-2-methoxypyridine dihydrochloride (20 g, 94.3 mmol) in water (200 mL). The mixture was stirred for 2 hour and adjusted pH to 7. The solvent was removed under reduced pressure and obtained crude powder to give 2-(6-methoxypyridin-3-yl)hydrazinecarboxamide. (25.4 g, 148% yield).

1H NMR (DMSO-d6, ppm) δ 3.75 (3H, s), 5.99 (2H, br s), 6.68 (1H, d, J=8.8 Hz), 7.12 (1H, dd, J=2.9, 8.7 Hz), 7.41 (1H, brs), 7.60 (1H, d, J=2.8 Hz), 7.77 (1H, s), (2) To a suspension of 2-(6-methoxypyridin-3-yl) hydrazinecarboxamide (17 g, 93.3 mmol) in 100 mL of toluene, pyridine (15.1 mL, 187 mmol) and then a solution of 4-methoxybenzoyl chloride (15.9 g, 93.3 mmol) in 50 mL of toluene were added. The mixture was refluxed with stirring for 1 hour. After cooling at 80° C., 75 mL of water was added to the mixture. After vigorous shaking, an insoluble material was isolated by filtration, washed with water and toluene, dried in vacuo to give 2-(4-methoxybenzoyl)-2-(6-methoxypyridin-3-yl) hydrazinecarboxamide (8.5 g, 28.8% yield).

1H NMR (DMSO-d6, ppm) δ 3.79 (3H, s), 3.83 (3H, s), 6.18 (2H, br s), 6.84 (1H, d, J=8.8 Hz), 6.93 (2H, d, J=8.7 Hz), 7.54 (2H, br d, J=8.5 Hz), 7.68–7.82 (1H, m), 8.15 (1H, br s), 8.98 (1H, br s), MS (ESI, m/e) 317 (M+1).

(3) A mixture of 2-(4-methoxybenzoyl)-2-(6-methoxypyridin-3-yl)hydrazinecarboxamide (1.0 g, 3.16 mmol) in 10% sodium hydroxide solution (2 mL)-ethanol (3mL) was heated at 60° C. for 1.5 hours. After cooling, the solvent was removed under reduced pressure. Water was added to the residue and the mixture was adjusted pH to ca. 4 to 5. A generated precipitate was isolated by filtration, washed with water and small amount of ethyl acetate, dried in vacuo to give 5-(4-methoxyphenyl)-1-(6-methoxypyridin-3-yl)-1H-1,2,4-triazol-3-ol (685 mg, 72.6% yield).

1H NMR (DMSO-d6, ppm) δ 3.77 (3H, s), 3.89 (3H, s), 6.87–7.05 (3H, m), 7.28–7.47 (2H, m), 7.74 (1H, dd, J=2.6, 8.8 Hz), 8.19 (1H, d, J=2.5 Hz), 11.38 (1H, br s), MS (ESI, m/e) 299 (M+1).

(4) A mixture of 5-(4-methoxyphenyl)-1-(6-methoxypyridin-3-yl)-1H-1,2,4-triazol-3-ol (300 mg, 1.01 mmol), potassium carbonate (417 mg, 3.02 mmol), and 2-iodo-1,1,1-trifluoroethane (0.496 mL, 5.03 mmol) in dimethyl sulfoxide (1.5 mL) were heated at 100° C. for 1 hour. After cooling, ice water and ethyl acetate were poured into the mixture and the organic layer was separated, washed with brine, and dried over magnesium sulfate. The solvent was removed under reduced pressure. The residue was purified by column chromatography (toluene-ethyl acetate 8:1) The desired product was washed with hexane to give 2-methoxy-5-(5-(4-methoxyphenyl)-3-(2,2,2-trifluoroethoxy)-1H-1,2,4-triazol-1-yl)pyridine (175 mg, 45.8% yield).

1H NMR (CDCl3, ppm) δ 3.82 (3H, s), 3.97 (3H, s), 4.75 (2H, q, J=8.2 Hz), 6.75–6.93 (3H, m), 6.38–7.50 (2H, m), 7.57 (1H, dd, J=2.6, 8.8 Hz), 8.16 (1H, d, J=2.5 Hz), MS (ESI, m/e) 381 (M+1).

mp 63.0–64.0° C.

EXAMPLE 16

Dimethylcarbamic chloride was added to a mixture of 1,5-bis(4-methoxyphenyl)-1H-1,2,4-triazol-3-ol (200 mg, 0.673 mmol) and pyridine (0.114 ml, 1.41 mmol) in dichloromethane (5 ml). Then the solution was stirred at 45° C. for 17 hours. Water and ethyl acetate were poured into the mixture and the organic layer was separated, washed with water and brine, and dried over magnesium sulfate. The solvent was removed under reduced pressure. The residue was purified by column chromatography (hexane-ethyl acetate 1:2). The desired product was washed with isopropyl ether to give 1,5-bis(4-methoxyphenyl)-1H-1,2,4-triazol-3-yl dimethylcarbamate. (88 mg, 35.5% yield)

1H NMR (CDCl3, ppm) δ 3.03 (3H, s), 3.14 (3H, s), 3.81 (3H, s), 3.85 (3H, s), 6.75–6.99 (4H, m), 7.20–7.38 (2H, m), 7.39–7.52 (2H, m), MS (ESI, m/e) 369 (M+1).

mp 121–123° C.

EXAMPLE 17

Potassium carbonate (279 mg, 2.02 mmol) was added to a solution of 1,5-bis(4-methoxyphenyl)-1H-1,2,4-triazol-3-ol (200 mg, 0.673 mmol) in dimethylformamide (2 mL). After 5 minute stirring, 3-bromo-1-propyne (0.18 mL, 2.02 mmol) was added to the mixture and the mixture was stirred for 4 hours. Ethyl acetate and water were poured into the mixture. The organic layer was separated, washed with water and brine, and dried over magnesium sulfate. The solvent was removed under reduced pressure. The residue was purified by silica gel column chromatography (toluene-ethyl acetate 4:1). The desired product was washed with isopropyl ether, isolated by filtration, and dried in vacuo to give 1,5-bis(4-methoxyphenyl)-3-(2-propynyloxy)-1H-1,2, 4-triazole (99 mg, 43.9% yield).

1H NMR (CDCl3, ppm) δ 2.53 (1H, t, J=2.4 Hz), 3.80 (3H, s), 3.85 (3H, s), 4.99 (2H, d, J=2.4 Hz), 6.75–6.88 (2H, m), 6.88–7.00 (2H, m), 7.18–7.36 (2H, m), 7.36–7.50 (2H, m), MS (ESI, m/e) 336 (M+1).

mp 81–82° C.

EXAMPLE 18

Potassium carbonate (279 mg, 2.02 mmol) and potassium iodide (335 mg, 2.02 mmol) was added to a solution of 1,5-bis(4-methoxyphenyl)-1H-1,2,4-triazol-3-ol (200 mg, 0.673 mmol) in dimethylformamide (2 mL). After 5 minutes stirring, 3-(chloromethyl)-1,2,4-oxadiazole (239 mg, 2.02 mmol) was added to the mixture and the mixture was heated at 100° C. for 1 hour. After cooling, ethyl acetate and water were poured into the mixture. The organic layer was separated, washed with water and brine, and dried over magnesium sulfate. The solvent was removed under reduced pressure. The residue was purified by preparative-TLC (toluene-ethyl acetate 4:1). The desired product was triturated with isopropylether, isolated by filtration, and dried in vacuo to give 3-({[1,5-bis(4-methoxyphenyl)-1H-1,2,4-triazol-3-yl]oxy}methyl)-1,2,4-oxadiazole (110 mg, 43.1% yield).

1H NMR (CDCl3, ppm) δ 3.80 (3H, s), 3.85 (3H, s), 5.59 (2H, s), 6.75–6.85 (2H, m), 6.85–7.05 (2H, m), 7.20–7.35 (2H, m), –7.50 (2H, m), 8.76 (1H, s), MS (ESI, m/e) 380 (M+1).

EXAMPLE 19

1,5-bis(4-methoxyphenyl)-3-[(5-methyl-3-isoxazolyl) methoxy]-1H-1,2,4-triazole (148 mg, 56.1% yield) was prepared from 1,5-bis(4-methoxyphenyl)-1H-1,2,4-triazol-3-ol and 3-(chloromethyl)-5-isoxazole by a similar manner described for Example 18.

1H NMR (CDCl3, ppm) δ 2.44 (3H, s), 3.81 (3H, s), 3.85 (3H, s), 5.43 (2H, s), 6.22 (1H, s), 6.75–6.89 (2H, m), 6.89–7.00 (2H, m), 7.21–7.36 (2H, m), 7.36-(2H, m), MS (ESI, m/e) 393 (M+1).

EXAMPLE 20

1,5-bis(4-methoxyphenyl)-3-(1,3-thiazol-4-ylmethoxy)-1H-1,2,4-triazole (132 mg, 49.7% yield) was prepared from 1,5-bis(4-methoxyphenyl)-1H-1,2,4-triazol-3-ol and 4-(chloromethyl)-1,3-thiazole hydrochloride by the similar manner described for Example 18.

1H NMR (CDCl3, ppm) δ 3.81 (3H, s), 3.85 (3H, s), 5.61 (2H, s), 6.75–7.02 (4H, m), 7.20–7.38 (2H, m), 7.38–7.50 (2H, m), 7.54 (1H, d, J=0.9 Hz), 8.82 (1H, d, J=2.0 Hz), MS (ESI, m/e) 395 (M+1).

EXAMPLE 21

2-{[1,5-bis(4-methoxyphenyl)-1H-1,2,4-triazol-3-yl]oxy}-N,N-dimethylacetamide (467 mg, 72.6% yield) was prepared from 1,5-bis(4-methoxyphenyl)-1H-1,2,4-triazol-3-ol and 2-chloro-N,N-dimethylacetamide by the similar manner described for Example 18.

1H NMR (CDCl3, ppm) δ 3.00 (3H, s), 3.07 (3H, s), 3.80 (3H, s), 3.84 (3H, s), 5.01 (2H, s), 6.75–7.00 (4H, m), 7.20–7.35 (2H, m), 7.35–7.49 (2H, m), MS (ESI, m/e) 383 (M+1).

EXAMPLE 22

1,5-bis(4-methoxyphenyl)-3-(2-butynyloxy)-1H-1,2,4-triazole (96 mg, 40.8% yield) was prepared from 1,5-bis(4-methoxyphenyl)-1H-1,2,4-triazol-3-ol and 1-bromo-2-butyne by the similar manner described for Example 18.

1H NMR (CDCl3, ppm) δ 1.88 (3H, t, J=2.3 Hz), 3.80 (3H, s), 3.84 (3H, s), 4.94 (2H, q, J=2.2 Hz), 6.78–6.85 (2H, m), 6.87–6.97 (2H, m), 7.22–7.32 (2H, m), 7.38–7.47 (2H, m), MS (ESI, m/e) 350 (M+1).

EXAMPLE 23

1,5-bis(4-methoxyphenyl)-3-(2-propoxy)-1H-1,2,4-triazole was prepared from 1,5-bis(4-methoxyphenyl)-1H-1,2,4-triazol-3-ol by the similar manner as that described for Example 13.

1H NMR (DMSO-d6, ppm) δ 7.33 (d, J=8.9 Hz, 2H), 7.30 (d, J=8.9 Hz, 2H), 7.02 (d, J=8.9 Hz, 2H), 6.93 (d, J=8.9 Hz, 2H), 4.9 (sept, J=6.1 Hz, 1H), 3.80 (s, 3H), 3.76 (s, 3H), 1.35 (d, J=6.1 Hz, 6H).

MS (ESI, m/e) 340 (M+1).

EXAMPLE 24

A mixture of 1,5-bis(4-methoxyphenyl)-1H-1,2,4-triazol-3-ol (0.3 g, 1.01 mmol) and potassium carbonate (418 mg, 3.03 mmol) in bromofluoromethane (1 mL)-dimethylformamide (3 mL) was heated at 100° C. with stirring for 3.5 hours. After cooling, ethyl acetate and water were poured into the mixture. The organic layer was separated, washed with water and brine, and dried over magnesium sulfate. The solvent was removed under reduced pressure. The residue was purified by silica gel column chromatography (hexane-ethyl acetate). The desired product was triturated with hexane, isolated by filtration, and dried in vacuo to give 1,5-bis(4-methoxyphenyl)-3-(fluoromethoxy)-1H-1,2,4-triazole.

1H NMR (DMSO-d6, ppm) δ 7.3–7.4 (m, 4H), 7.05 (d, J=9.0 Hz, 2H), 6.95 (d, J=8.9 Hz, 2H), 6.02 (d, J=52.4 Hz, 2H), 3.81 (s, 3H), 3.76 (s, 3H).

MS (ESI, m/e) 330 (M+1).

EXAMPLE 25

1,5-bis(4-methoxyphenyl)-3-cyclohexyloxy-1H-1,2,4-triazole was prepared from 1,5-bis(4-methoxyphenyl)-1H-1,2,4-triazol-3-ol by the similar manner as that described for Example 13.

1H NMR (DMSO-d6, ppm) δ 7.2–7.4 (m, 4H), 7.02 (d, J=8.8 Hz, 2H), 6.98 (d, J=8.8 Hz, 2H), 4.66 (m, 1H), 3.80 (s, 3H), 3.75 (s, 3H), 1.9–2.1 (m, 2H), 1.2–1.9 (m, 8H).

MS (ESI, m/e) 380 (M+1).

EXAMPLE 26

1,5-bis(4-methoxyphenyl)-3-(4-chlorophenylmethoxy)-1H-1,2,4-triazole was prepared from 1,5-bis(4-methoxyphenyl)-1H-1,2,4-triazol-3-ol by the similar manner as that described for Example 13.

1H NMR (DMSO-d6, ppm) δ 7.4–7.6 (m, 4H), 7.3–7.5 (m, 2H), 7.03 (d, J=8.9 Hz, 2H), 6.94 (d, J=8.9 Hz, 2H), 5.32 (s, 2H), 3.81 (s, 3H), 3.76 (s, 3H).

MS (ESI, m/e) 422 (M+1).

EXAMPLE 27

1,5-bis(4-methoxyphenyl)-3-cyanomethoxy-1H-1,2,4-triazole was prepared from 1,5-bis(4-methoxyphenyl)-1H-1,2,4-triazol-3-ol by the similar manner as that described for Example 13.

1H NMR (DMSO-d6, ppm) δ 7.3–7.4 (m, 4H), 7.05 (d, J=8.9 Hz, 2H), 6.96 (d, J=8.8 Hz, 2H), 5.27 (s, 2H), 3.81 (s, 3H), 3.76 (s, 3H).

MS ESI, m/e) 337 (M+1).

EXAMPLE 28

(1) To a solution of dimethylcyanamide (10.0 g, 142.7 mmol) in methanol (50 mL) was added dropwise sulfuric acid (14.0 g, 142.7 mmol) over 2 hours at 20–30° C. The mixture was stirred at 20–30° C. for 4 hours and then concentrated in vacuo. To the residue was added acetone (50 mL) and stirred at 20–30° C. After crystallized, the mixture was stirred at 20–30° C. for 30 minutes, then at 0–10° C. for 1 hour and filtered. The crystals were washed with acetone (20 mL) and dried in vacuo to give N,N,O-trimethylisourea sulfate (22.86 g, 80.0% yield) as white granulated solids.

1H NMR (DMSO d6, ppm) δ 2.98 (3H, br), 3.01 (3H, br), 4.01 (3H, s), 8.66 (2H, br).

(2) To a cooled (0–15° C.) solution of N,N,O-trimethylisourea sulfate (20.0 g, 99.9 mmol) in a mixture of methanol (100 mL) and water (1.8 mL) was added dropwise 28% sodium methoxide in methanol (38.55 g, 199.8 mmol) over 2 hours at 20–30° C. and stirred at the ambient temperature for 1 hour. The resulting precipitate was filtered off and washed with methanol (40 mL). The filtrate was concentrated in vacuo and ethyl acetate (180 mL) and triethylamine (10.11 g, 99.9 mmol) were added to the residue. To the mixture was added dropwise a solution of 4-methoxybenzoylchloride (16.15 g, 94.9 mmol) in ethyl acetate (20 mL) over 2 hour, at 20–30° C. and then stirred at the same temperature for 2 hours. To the reaction mixture was added water (40 mL) and the aqueous layer was extracted with ethyl acetate (100 mL). The combined organic layers were concentrated in vacuo and 4-methoxyphenylhydradine hydrochloride (17.44 g, 99.9 mmol), methanol (120 mL) and acetic acid (10 mL) were added to the residue. To the mixture was added dropwise triethylamine (10.11 g, 99.9 mmol) and stirred at 20–30° C. for 3 hours then at 40–50° C. for additional 3 hours. The reaction mixture was cooled to 20–30° C. and stirred for 30 minutes. To the mixture was added dropwise water (120 mL) and stirred for 1 hour. The crystals were filtered, washed with 50% aqueous methanol (40 mL) and dried in vacuo to give crude 3-methoxy-1,5-bis(4-methoxyphenyl)-1H-1,2,4-triazole (20.36 g, 65.5% yield) as pale brownish yellow needles.

(3) To the stirred purified water (100 mL) was added dropwise a solution of 3-methoxy-1,5-bis(4-methoxyphenyl)-1H-1,2,4-triazole (20.0 g, 64.2 mmol) obtained above in acetone (300 mL) and stirred at 20–30° C. for 30 minutes. The mixture was concentrated to ~200 mL in vacuo, stirred at 35–45° C. for 1 hour then at 20–30° C. for 1 hour and filtered. The crystals were washed with 50% aqueous acetone (40 mL) and dried in vacuo to give pure 3-methoxy-1,5-bis(4-methoxyphenyl)-1H-1,2,4-triazole (18.36 g, 91.8% yield) as colorless needles.

Representative X-ray powder diffraction Peaks (2 θ):

9.1°, 15.4°, 19.7°
mp 125° C.

List of the Compounds Produced by the Examples (I)

| Example No. | $(X)_m$ | $R^1$ | $R^2$ | $R^3$ | Y | Z |
|---|---|---|---|---|---|---|
| 1-(2) | — | —CF$_3$ | —OCH$_3$ | —OCH$_3$ | —CH— | —CH— |
| 2 | — | —CF$_3$ | —CH$_3$ | —OCH$_3$ | N | —CH— |
| 3 | — | —CF$_3$ | —CN | —OCH$_3$ | —CH— | —CH— |
| 4 | — | —CF$_3$ | —CH$_3$ | —OCH$_3$ | —CH— | —CH— |
| 5-(4) | O | —CH$_3$ | —OCH$_3$ | —OCH$_3$ | —CH— | —CH— |
| 6-(4) | S | —CH$_3$ | OCH$_3$ | OCH$_3$ | —CH— | CH— |
| 6-(5) | SO | —CH$_3$ | —OCH$_3$ | —OCH$_3$ | —CH— | —CH— |
| 6-(6) | SO$_2$ | —CH$_3$ | —OCH$_3$ | OCH$_3$ | —CH— | —CH— |
| 7 | — | —CF$_3$ | —OCH$_3$ | —CH— | —CR | |
| 8 | — | —CF$_3$ | —OCH$_3$ | —OCH$_3$ | N | —CH— |
| 9-(2) | — | —CF$_3$ | —OCH$_3$ | —CN | —CH— | —CR |
| 10 | O | —C$_2$H$_5$ | —OCH$_3$ | —OCH$_3$ | —CH— | —CH— |
| 11-(2) | — | —CF$_3$ | —OCH$_3$ | —CH$_3$ | —CH— | —CH— |
| 12-(2) | — | —CF$_3$ | —OCH$_3$ | —OCH$_3$ | —CH— | N |
| 13 | O | —CH$_2$—CF$_3$ | —OCH$_3$ | —OCH$_3$ | —CH— | —CH— |
| 14-(3) | O | —CH$_2$—CF$_3$ | —OCH$_3$ | —OCH$_3$ | N | —CH— |
| 15-(4) | O | —CH$_2$—CF$_3$ | —OCH$_3$ | —OCH$_3$ | —CH— | N |
| 16 | O | —CO-N(CH$_3$)$_2$ | —OCH$_3$ | —OCH$_3$ | —CH— | —CH— |
| 17 | O |  | —OCH$_3$ | —OCH$_3$ | —CH— | —CH— |
| 18 | O |  | —OCH$_3$ | —OCH$_3$ | —CH— | —CH— |
| 19 | O |  | —OCH$_3$ | —OCH$_3$ | —CH— | —CH— |
| 20 | O |  | —OCH$_3$ | —OCH$_3$ | —CH— | —CH— |
| 21 | O | —CH$_2$—CO—N(CH$_3$)$_2$ | —OCH$_3$ | —OCH$_3$ | —CH— | —CH— |
| 22 | O |  | —OCH$_3$ | —OCH$_3$ | —CH— | —CH— |
| 23 | O | —CH(CH$_3$)$_2$ | —OCH$_3$ | —OCH$_3$ | —CH— | —CH— |
| 24 | O | —CH$_2$—F | —OCH$_3$ | —OCH$_3$ | —CH— | —CH— |

-continued (I)

| Example No. | $(X)_m$ | $R^1$ | $R^2$ | $R^3$ | Y | Z |
|---|---|---|---|---|---|---|
| 25 | O | 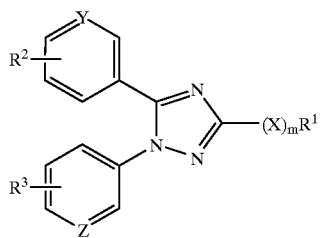 | —OCH$_3$ | —OCH$_3$ | —CH— | —CH— |
| 26 | O | (4-chlorobenzyl) | —OCH$_3$ | —OCH$_3$ | —CH— | —CH— |
| 27 | O | —CH$_2$—CN | —OCH$_3$ | —OCH$_3$ | —CH— | —CH— |
| 28-(3) | O | —CH$_3$ | —OCH$_3$ | —OCH$_3$ | —CH— | —CH— |

What is claimed is:

1. A compound of the formula (I):

(I)

wherein $R^1$ is lower alkyl which is optionally substituted with halogen, Cyano, N,N-di(lower)alkylcarbamoyl or phenyl optionally substituted with halogen $R^2$ is lower alkyl, lower alkoxy, or cyano;

$R^3$ is lower alkyl, lower alkoxy, or cyano;

X is O;

Y and Z are each CH; and m is 1;

or a salt thereof.

2. The compound of claim 1, wherein $R^1$ is lower alkyl, lower alkyl substituted with halogen, cyano, or N,N-di(lower)alkylcarbamoyl;

$R^2$ is lower alkoxy;

$R^3$ is lower alkoxy;

X is O; Y and Z are each CH; and m is 0 or 1.

3. The compound of claim 2, wherein $R^1$ is lower alkyl or lower alkyl substituted with halogen;

$R^2$ is lower alkoxy;

$R^3$ is lower alkoxy;

X is O; Y and Z are each CH; and m is 1.

4. The compound of claim 3, wherein $R^1$ is lower alkyl.

5. The compound of claim 1, which is 3-methoxy-1,5-bis (4-methoxyphenyl)-1H-1,2,4-triazole.

6. A process for preparing a compound (I), (I)

wherein $R^1$ is lower alkyl which is optionally substituted with halogen, cyano, N,N-di(lower)alkylcarbamoyl, or phenyl optionally substituted with halogen;

$R^2$ is lower alkyl, lower alkoxy, or cyano;

$R^3$ is lower alkyl, lower alkoxy, or cyano;

X is O;

Y and Z are each CH; and m is 1;

or a salt thereof, which comprises reacting a compound (VI) of a following formula:

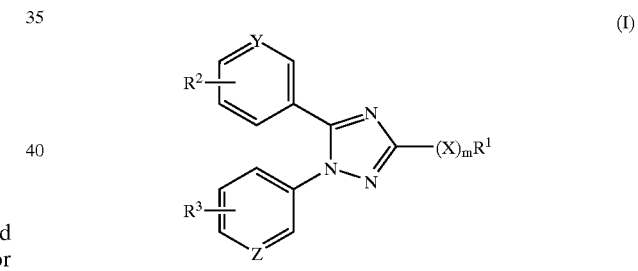

wherein $R^1$, X and m are each as defined above, or a salt thereof, with a compound (VII) of a following formula:

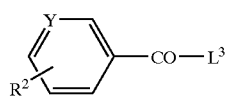

(VII)

wherein $R^2$ and Y are each as defined above, and $L^3$ is a leaving group,
or a salt thereof to give a compound (VIII) of a following formula:

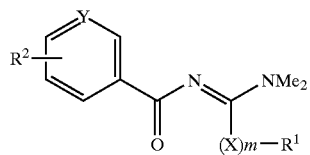

(VIII)

wherein $R^1$, $R^2$, X, Y and m are each as defined above, or a salt thereof, and further reacting with a compound of (IX) of a following formula:

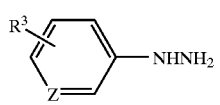

(IX)

wherein $R^3$ and Z are each as defined above,
or a salt thereof to give a compound (I) or a salt thereof.

7. A pharmaceutical composition comprising the compound (I) of claim 1 or a salt thereof, as an active ingredient, and a pharmaceutically non-toxic carrier or excipient.

8. A method of treating pains caused by or associated with osteoarthritis comprising administering to a patient in need thereof an effective amount of the compound of claim 1 or a salt thereof.

9. A pharmaceutical composition comprising the compound of claim 5 or a salt thereof; and a pharmaceutically non-toxic carrier or excipient.

10. A method of treating pains caused by or associated with osteoarthritis comprising administering to a patient in need thereof an effective amount of the compound of claim 5 or a salt thereof.

* * * * *